United States Patent
Kohno

(10) Patent No.: US 7,297,405 B2
(45) Date of Patent: Nov. 20, 2007

(54) MAGNETIC PARTICLES HAVING CORE-SHELL STRUCTURE

(75) Inventor: Hideki Kohno, Tokyo (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 10/490,742

(22) PCT Filed: Oct. 11, 2002

(86) PCT No.: PCT/JP02/10590

§ 371 (c)(1),
(2), (4) Date: Apr. 9, 2004

(87) PCT Pub. No.: WO03/033159

PCT Pub. Date: Apr. 24, 2003

(65) Prior Publication Data

US 2004/0241428 A1     Dec. 2, 2004

(30) Foreign Application Priority Data

Oct. 11, 2001    (JP)    ............................. 2001-313974

(51) Int. Cl.
*B32B 5/16*    (2006.01)
*B05D 7/00*    (2006.01)
(52) U.S. Cl. ...................... 428/403; 427/221; 427/220; 427/226; 427/372.2; 428/407; 428/900
(58) Field of Classification Search ................ 428/407, 428/900, 403; 435/72, 182, 173.1, 173.9; 424/492, 497; 427/221, 220, 226, 372.2
See application file for complete search history.

(56) References Cited

U.S. PATENT DOCUMENTS

| 3,892,673 | A | * | 7/1975 | Ehrreich et al. | .......... 252/62.54 |
| 4,342,739 | A | * | 8/1982 | Kakimi et al. | ............... 435/7.9 |
| 4,452,773 | A | * | 6/1984 | Molday | ..................... 424/1.37 |
| 4,612,247 | A | * | 9/1986 | Walsh et al. | ................. 428/402 |
| 5,262,176 | A | * | 11/1993 | Palmacci et al. | ......... 424/9.322 |
| 5,597,531 | A | * | 1/1997 | Liberti et al. | ................. 422/57 |
| 6,123,920 | A | * | 9/2000 | Gunther et al. | .......... 424/9.322 |
| 6,706,288 | B2 | * | 3/2004 | Gustavsson et al. | ........ 424/497 |
| 6,761,877 | B2 | * | 7/2004 | Barbera-Guillem | ......... 424/9.6 |

FOREIGN PATENT DOCUMENTS

| JP | 5-99926 | 4/1993 |
| JP | 11-191509 | 7/1999 |
| JP | 11-191510 | 7/1999 |
| WO | 98/34114 | 8/1998 |

* cited by examiner

*Primary Examiner*—H. T Le
(74) *Attorney, Agent, or Firm*—Oblon, Spivak, McClelland, Maier & Neustadt, P.C.

(57) ABSTRACT

Magnetic particles each including particulate magnetic material and a readily decomposable or easily soluble polymer coating layer containing a reactive component, the coating layer being disposed on the surface of the magnetic material; and a method for producing a reaction product by use of the magnetic particles.

Employment of the magnetic particles of the present invention allows solid phase reaction to proceed efficiently and attains an easy recovery of reaction product.

18 Claims, 2 Drawing Sheets

MAGNETIC PARTICLES HAVING CORE-SHELL STRUCTURE

TECHNICAL FIELD

The present invention relates to magnetic particles which can provide reaction fields having high reaction efficiency and allow reaction products to be readily separated and recovered; and to a method for producing reaction products by use of the magnetic particles.

BACKGROUND ART

In reaction systems utilizing microorganisms, such as a wastewater treatment system and a system by which pharmaceuticals are produced by use of microorganisms, microorganisms are either directly added to a reaction mixture system or immobilized through a immobilization technique. When microorganisms are directly added to a reaction mixture system, reaction efficiency becomes generally lower. Also, in cases where immobilized microorganisms are employed, a substrate solution is usually allowed to pass through the immobilized microorganism phase, where the following problems are noted: insufficient contact time between the substrate and the microorganisms, or when the contact time is prolonged to a sufficient level, reaction efficiency is reduced. Therefore, from the viewpoint of reaction efficiency, direct addition of immobilized microorganisms into a reaction mixture is desired.

However, when immobilized microorganisms are directly added to a reaction system, not only does solid-liquid separation become difficult after completion of reaction, but separation and recovery of a reaction product; i.e., the target product, also become difficult. This is because the reaction mixture contains not only the reaction product, but also the starting materials, medium components, etc. Moreover, reactions making use of microorganisms and antigen-antibody reactions cannot proceed endlessly even when starting materials are added continuously. Indeed, since the reaction is eventually saturated, maintaining high reaction efficiency is difficult.

Accordingly, an object of the present invention is to provide means for realizing a reaction field of high reaction efficiency and facilitating separation and recovery of reaction product.

DISCLOSURE OF THE INVENTION

The present inventor has found that magnetic particles produced by coating the surfaces of magnetic particulate cores with a readily decomposable or easily soluble polymer to which a reactive component such as microorganism, antigen, antibody, enzyme, or receptor has been incorporated allow reaction to proceed in the coating layer, and that the reaction is more efficient than when attained in a liquid phase. Moreover, after completion of reaction, solid-liquid separation can be easily performed by controlling magnetic force, making recovery of the resultant reaction product easy and efficient. The present invention has been achieved on the basis of these findings.

Accordingly, the present invention provides a magnetic particle including particulate magnetic material and a readily decomposable or easily soluble polymer coating layer containing a reactive component, the coating layer being disposed on the surface of the magnetic material.

The present invention also provides a method for producing a reaction product, characterized by allowing the magnetic particle of the invention to react with a substance capable of reacting with the aforementioned reactive component, separating the magnetic particle from the reaction system under control of magnetic force, and subsequently decomposing or dissolving the readily decomposable or easily soluble polymer, to thereby recover the reaction product.

BEST MODE FOR CARRYING OUT THE INVENTION

Figure 1:
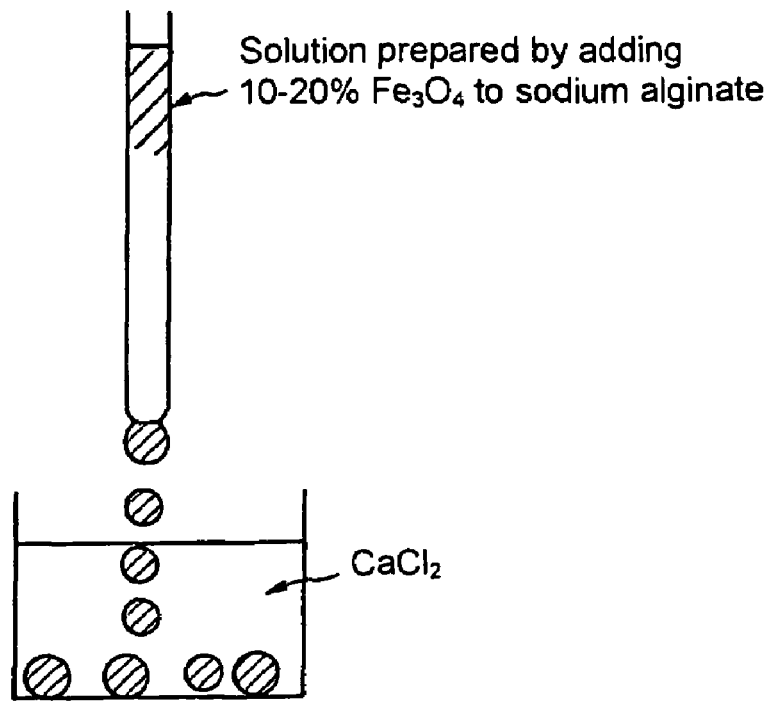
FIG. 1 shows a method for producing the particulate magnetic material.

The magnetic particle of the present invention is formed of a core and a shell. The core is made of a particulate magnetic material, and the shell is made of a readily decomposable or easily soluble polymer containing a reactive component. The particulate magnetic material may be a magnetic material per se, or may be in the form of a coated particle—the coat may be gelatinized—prepared by coating the magnetic material with non-reactive organic polymer or an inorganic substance in advance. Examples of preferred magnetic materials include iron and magnetic iron oxide. Examples of the non-reactive organic polymer include polystyrene, latex, divinylbenzene latex, sodium alginate, and carrageenan. Examples of the non-reactive inorganic substance include ceramic, silica, alumina, silica-alumina, and charcoal powder. The size of the particulate magnetic material ranges from 0.1 μm to 20 mm, and is preferably 0.2 μm to 20 mm. The magnetic material may be spherical, generally spherical, square, or may have any other shape, so long as it assumes the form of a particle.

Given the readily decomposable or easily soluble polymer which serves as the coating layer of the magnetic particle of the present invention is not decomposed or dissolved during reaction, but is decomposed or dissolved after solid-liquid separation following completion of reaction, the polymer is preferably decomposed or dissolved under conditions different from those under which reaction of reactive component takes place.

Examples of such polymers include the following polymers: when the reaction component is reactive under alkaline conditions, polymers which are decomposed or dissolved specifically under acidic conditions; when the reaction component is reactive under acidic conditions, polymers which are decomposed or dissolved specifically under alkaline conditions; and when the reaction component is reactive under physiological conditions; e.g., at 30 to 40° C., polymers which are decomposed or dissolved at a temperature higher than such a temperature range, for example, at a temperature of 50° C. or more.

More preferably, the readily decomposable or easily soluble polymer is a gel-formable polymer. Among a variety of gel-formable polymers, there may be selected polymers which can be transformed into a sol under acidic conditions; polymers which can be transformed into a sol under alkaline conditions; or polymers which can be transformed into a sol under temperature changes. Of these, preferred are polymers which can be transformed into a gel under temperature changes, such as polysaccharides including agar and calcium alginate; proteins such as gelatin; and synthetic polymers such as acrylic amides. From the viewpoints of availability and readiness to dissolve under heating at about 50° C. or more, agar and similar gel-formable polysaccharides are particularly preferred. These polymers may be used singly or in combination of two or more species.

No particular limitations are imposed on the reactive component of the present invention. Preferred reactive components are those which can be reacted under physiological conditions, such as antigens, antibodies, receptors, enzymes, and microorganisms. Of these, antigens, antibodies, receptors, enzymes, and microorganisms are more preferred.

Examples of antigens and antibodies include various biological components, and monoclonal or polyclonal antibodies thereto. Examples of enzymes include those derived from animals, plants, or microorganisms. Examples of microorganisms include bacteria, eumycetes, yeasts, basidiomysetes, and viruses.

Of these reactive components, microorganisms are particularly preferred. Examples of the microorganisms used in wastewater treatment include those belonging to genus *pseudomonas* (e.g., *Pseudomonas denitrificans*), genus *nitrobacter* (e.g., *Nitrobacter agilis*), genus *nitrosomonas* (e.g., *Nitrosomonas europaea*), or to genus *alcaligenes*, nitrifying bacteria, denitrifying bacteria, chlorella, and bacteria belonging to genus *citorobacter*. Examples of photosynthesis bacteria include bacteria belonging to genus *rhodobacter* (e.g., *Rhodobacter sphaeroides*). Examples of yeast include those belonging to genus *saccharomyces*.

In view of reaction efficiency, any of the reactive components is incorporated into a coating layer in an amount of 0.1 to 70 wt %, preferably 1 to 50 wt %, more preferably 1 to 30 wt %. The volume ratio of the amount of coating layer to the amount of the magnetic material of the core is 1/10 or more, preferably 1/10 to 10,000 times.

The magnetic particles of the invention may be produced, for example, by dropwise addition of a suspension containing readily decomposable or easily soluble polymer, a reactive component, and magnetic particles to medium which does not dissolve the polymer. The readily decomposable or easily soluble polymer may be coated as a double layer.

The method of producing the reactive component by use of the magnetic particles of the present invention is preferably carried out by allowing the magnetic particles to react with a substance that reacts with the aforementioned reactive component, separating the magnetic particles from the reaction system by use of magnetic control, and then recovering the reaction product by dissolving the readily decomposable or easily soluble polymer. Examples of the substance which reacts with the reactive component include antibody in the case where the reactive component is an antigen, antigen in the case where the reactive component is an antibody, a substrate in the case where the reactive component is an enzyme, and a binding substance in the case where the reactive component is a receptor. When the reactive component is bacteria, substances utilized by the bacteria, such as wastewater, factory wastewater, and industrial waste, can be used.

The reaction conditions are determined on the basis of relation between the reactive component and the reaction substance. For example, when bacteria, antigens, antibodies, etc. are employed as the reactive component, physiological conditions (room temperature to 40° C.) are preferred. Addition of the magnetic particles of the present invention to a liquid phase containing the reaction substance is convenient and preferred for starting reaction.

After completion of reaction, a magnetic field is applied to the outside; e.g., the side surface, of the container. The magnetic particles are attracted to the side surface. Thus, solid-liquid separation can be performed easily and efficiently. In this case, control of the magnetic force may be performed by bringing a paramagnetic material closer to the side surface. Alternatively, control of the magnetic force may be achieved by switching an electromagnet ON and OFF.

After solid-liquid separation, the magnetic particles are recovered and the aforementioned polymer is decomposed or dissolved, whereby the reaction product can be recovered very easily.

It should be noted that when bacteria or enzymes are used as the reactive component, the reaction usually saturates and stops at a certain point. However, when some of the magnetic particles are removed by the magnetic control and new magnetic particles are supplied, the reaction proceeds further and reaction efficiency is drastically improved.

EXAMPLES

The present invention will next be described in more detail by way of examples, which should not be construed as limiting the invention thereto.

Example 1

Sodium alginate (2 to 3 g) is dissolved in pure water(100 mL) under heating. $Fe_3O_4$ (10 to 20 g) is added thereto, followed by sufficient stirring. The resultant solution is slowly added dropwise to 1% aqueouscalcium chloride solution under stirring, whereby magneticgel spheres (2 to 10 mm) can be obtained (FIG. 1). The resultant magnetic gel sphere can be employed as the core of the magnetic particle of the present invention.

Example 2

Figure 2:
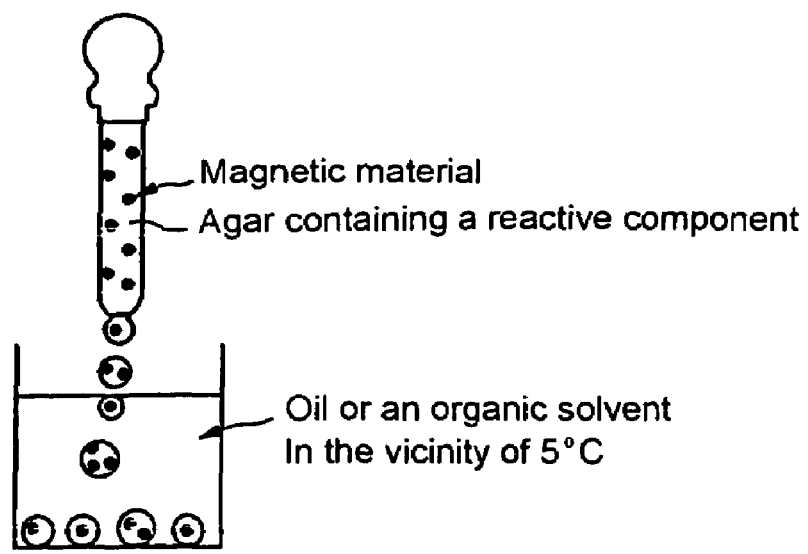
FIG. 2 shows an example method for producing the magnetic particle of the present invention.

Gelatin powder (15 g) is dissolved in ultra pure water (150 mL) under heating. Separately, photosynthetic bacteria (*rhodobacter sphaeroides* RV) serving as a reactive component is added to ultra pure water (150 mL). The resultant solutions are mixed together. The solution mixture is maintained at about 50° C., and slowly added dropwise (e.g., at 50 droplets/minute) to oil or an organic solvent cooled at about 5° C., whereby gel spheres (2 to 15 mm in diameter) are obtained (FIG. 2). Each gel sphere contains one to three pieces of magnetic material (a magnet measuring about 5 mm in diameter).

Example 3

Figure 3:
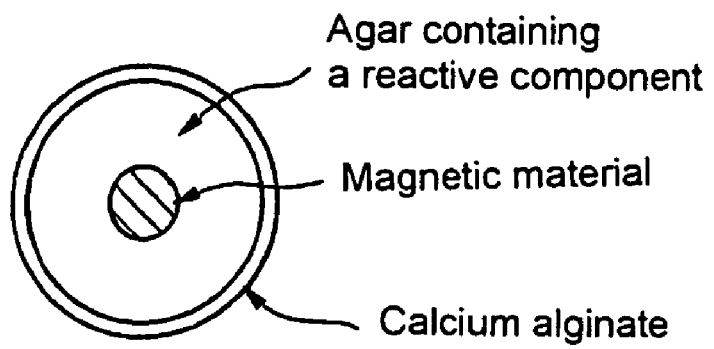
FIG. 3 is a diagram showing a three-layered magnetic particle of the present invention.
Figure 4:
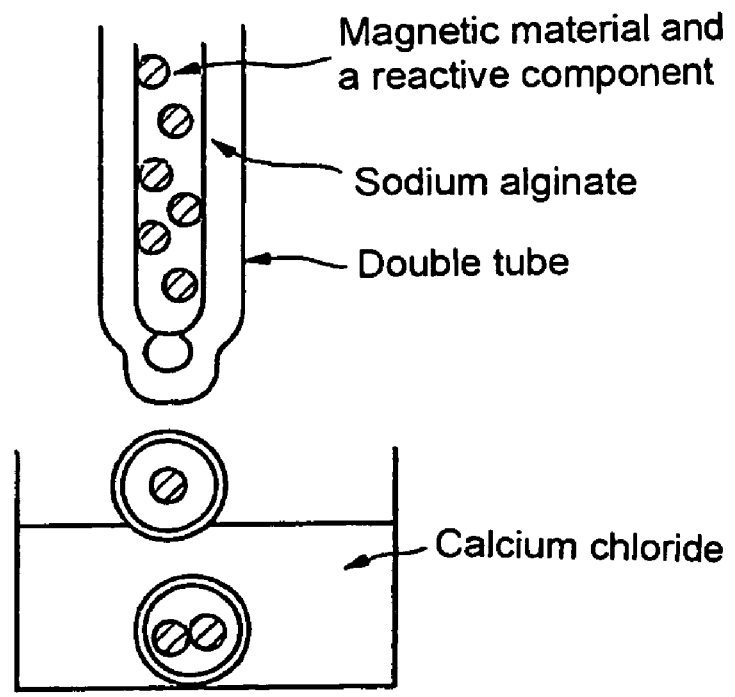
FIG. 4 shows a method for producing the three-layered magnetic particle of the present invention.

The same magnetic material as that employed in Example 2 is used as the core, and the core is covered with agar gel or sol, serving as the main layer, containing 2 to 7 wt. % photosynthetic bacteria (*rhodobacter sphaeroides* RV) as a reactive component. The agar gel or sol is wrapped with an outer film containing 2 wt. % calcium alginate to provide sufficient strength, whereby a three-layered gel sphere is obtained (FIG. 3). The gel sphere is produced as shown in FIG. 4 through use of a double tube and by way of addition dropwise to 1% calcium chloride solution, followed by cooling.

Example 4

Using magnetic particles of the present invention obtained by the same method as that employed in Example 2, generated hydrogen from organic acid caused by photosynthetic bacteria immobilized in the magnetic particles was examined. The number of cells contained in agar in the magnetic particles of the present invention was controlled so as to attain an optical turbidity of 2.0 at a wavelength of 660 nm. The concentration of the agar was 3%, and a buffer was employed instead of ultra pure water.

The bacteria in the magnetic particles of the present invention were cultured in a hydrogen-generating culture medium (containing 100-mM HEPES, 60-mM sodium lactate (substrate), and 10-mM sodium glutamate (nitrogen source substrate)) in an argon atmosphere under anaerobic conditions at 30° C. and under light (light intensity: 10 klux).

The amount of generated hydrogen was measured under the conditions shown in Table 1, while the pH values of the substrate solution and the agar gel were varied (300 hours).

TABLE 1

| | Substrate solution | | Agar | |
|---|---|---|---|---|
| | pH | buffer | pH | buffer |
| A | 6.8 | HEPES | — | $H_2O$ |
| B | 6.8 | HEPES | 6.8 | HEPES |
| C | 5.7 | MES | — | $H_2O$ |
| D | 5.7 | MES | 5.7 | MES |
| E | 8.5 | TAPS | — | water |
| F | 8.5 | TAPS | 8.5 | TAPS |

Effects on generation of hydrogen was examined under the conditions where pH value of the gel was the optimal value (6.8) and the pH values of the buffer were 6.8 (A), 5.7 (C, acidic side), and 8.5 (E, alkaline side). The total amounts of generated hydrogen were found to be 2,126 mL (A, pH 6.8), 1,722 mL (C, pH 5.7), and 2,186 mL (E, pH 8.5). The amounts of generated hydrogen for cases A (pH 6.8, optimal culture) and E (pH 8.5) were nearly the same. The amount of generated hydrogen for case C (pH 5.7) was 80% (20% reduction) that for case A (pH 6.8).

When the pH values in agar were adjusted with a buffer to the pH value of the substrate, the amounts of generated hydrogen were 1,260 mL (B, pH 6.8), 20 mL (D, pH 5.7), and 2,528 mL (F, pH 8.5), thereby demonstrating that hydrogen was not generated on the acidic side.

Comparison of the amounts of generated hydrogen for cases B (pH 6.8) and F (pH 8.5) revealed that the amount of hydrogen for case F (pH 8.5) is two times that for the optimal pH value (6.8). The amounts of generated hydrogen for cases A and B, C and D, and E and F, where the pH values of the substrate solutions were the same, were compared. The amount of generated hydrogen for case A was 1.7 times that for case B. The amount of generated hydrogen for case C was much greater than that for case D. The amount of generated hydrogen for case F was 1.3 times that for case E. The above results suggest that hydrogen can be generated on the acidic side when the pH value in agar is 6.8. When the pH value in agar is 8.5, the amount of generated hydrogen on the alkaline side is greater than that when the pH value in agar is 6.8. The above results show that a wider pH range is achieved for reaction in the magnetic particles of the present invention than for that in the mere substrate solution.

In addition to the above, reaction rate tended to be higher than that in the substrate solution.

After completion of reaction, the substrate solution and the magnetic particles could be easily separated from each other by placing a magnet on a wall of the container. The agar gel dissolved when the recovered magnetic particles were heated at about 50° C., and the magnetic material and the gel were successfully separated from each other.

INDUSTRIAL APPLICABILITY

Employment of the magnetic particles of the present invention allows solid phase reaction to proceed efficiently and attains an easy recovery of reaction product.

The invention claim is:

1. A magnetic particle in the form of a core and a shell, said particle having a size ranging from 2 to 20 mm, wherein the core is in particulate form and comprises particulate magnetic material, and the shell comprises a polymer coating layer containing a polymer and a reactive component, the coating layer being disposed on the surface of the core, wherein the polymer is decomposable or soluble under conditions different from those where the reactive component reacts, and wherein the reactive component and the polymer are different components.

2. The magnetic particle according to claim 1, wherein the different conditions are one of (1) when the reaction component is reactive under alkaline conditions, the polymer is decomposed or dissolved under acidic conditions; (2) when the reaction component is reactive under acidic conditions, the polymer is decomposed or dissolved under alkaline conditions; and (3) when the reaction component is reactive under physiological temperature conditions, the polymer is decomposed or dissolved at a temperature higher than such temperature conditions.

3. The magnetic particle according to claim 1, wherein the reactive component and the polymer are present as a physical mixture.

4. A method for producing a reaction product, comprising allowing the magnetic particle according to claim 1 to react with a substance capable of reacting with the reactive component, separating the magnetic particle from the reaction system under control of magnetic force, and subsequently decomposing or dissolving the polymer, to thereby recover the reaction product.

5. The magnetic particle according to claim 1, wherein the reactive component reacts under physiological conditions.

6. The magnetic particle according to claim 5, wherein the reactive component is an antigen, an antibody, a receptor, an enzyme, or a microorganism.

7. The magnetic particle according to claim 6, wherein the polymer is a gel-formable polymer.

8. A method for producing a reaction product, comprising allowing the magnetic particle according to claim 7 to react with a substance capable of reacting with the reactive component, separating the magnetic particle from the reaction system under control of magnetic force, and subsequently decomposing or dissolving the polymer, to thereby recover the reaction product.

9. A method for producing a reaction product, comprising allowing the magnetic particle according to claim 6 to react with a substance capable of reacting with the reactive component, separating the magnetic particle from the reaction system under control of magnetic force, and subsequently decomposing or dissolving the polymer, to thereby recover the reaction product.

10. The magnetic particle according to claim 5, wherein the polymer is a gel-formable polymer.

11. A method for producing a reaction product, comprising allowing the magnetic particle according to claim 10 to react with a substance capable of reacting with the reactive component, separating the magnetic particle from the reaction system under control of magnetic force, and subsequently decomposing or dissolving the polymer, to thereby recover the reaction product.

12. A method for producing a reaction product, comprising allowing the magnetic particle according to claim 5 to react with a substance capable of reacting with the reactive component, separating the magnetic particle from the reaction system under control of magnetic force, and subsequently decomposing or dissolving the polymer, to thereby recover the reaction product.

13. The magnetic particle according to claim 1, wherein the reactive component is an antigen, an antibody, a receptor, an enzyme, or a microorganism.

14. The magnetic particle according to claim 13, wherein the polymer is a gel-formable polymer.

15. A method for producing a reaction product, comprising allowing the magnetic particle according to claim 14 to react with a substance capable of reacting with the reactive component, separating the magnetic particle from the reaction system under control of magnetic force, and subsequently decomposing or dissolving the polymer, to thereby recover the reaction product.

16. A method for producing a reaction product, comprising allowing the magnetic particle according to claim 13 to react with a substance capable of reacting with the reactive component, separating the magnetic particle from the reaction system under control of magnetic force, and subsequently decomposing or dissolving the polymer, to thereby recover the reaction product.

17. The magnetic particle according to claim 1, wherein the polymer is a gel-formable polymer.

18. A method for producing a reaction product, comprising allowing the magnetic particle according to claim 17 to react with a substance capable of reacting with the reactive component, separating the magnetic particle from the reaction system under control of magnetic force, and subsequently decomposing or dissolving the polymer, to thereby recover the reaction product.

* * * * *